United States Patent [19]

Giardina et al.

[11] Patent Number: 4,806,547

[45] Date of Patent: Feb. 21, 1989

[54] ISOQUINOLINE DERIVATIVES, ANALGESIC COMPOUNDS THEREOF AND METHOD OF TREATING PAIN

[75] Inventors: Giuseppe Giardina; Vittorio Vecchietti, both of Milan, Italy

[73] Assignee: Dr. Lo. Zambeletti SPA, Italy

[21] Appl. No.: 6,068

[22] Filed: Jan. 22, 1987

[30] Foreign Application Priority Data

Jan. 24, 1986 [GB] United Kingdom ............... 8601796

[51] Int. Cl.$^4$ ................ A61K 31/47; C07D 401/06; C07D 217/16
[52] U.S. Cl. .................................. 514/307; 514/212; 540/597; 546/145; 546/146; 546/147
[58] Field of Search ............... 546/146, 147; 540/596; 514/307

[56] References Cited

U.S. PATENT DOCUMENTS

| | | | |
|---|---|---|---|
| 3,985,881 | 10/1976 | Meherhof et al. | 546/146 |
| 4,232,160 | 11/1980 | Schut et al. | 546/146 |
| 4,654,351 | 3/1987 | Bernath et al. | 546/147 |
| 4,753,952 | 6/1988 | Vecchietti et al. | 540/597 |

FOREIGN PATENT DOCUMENTS 0139066  8/1982  Japan ................. 546/146

OTHER PUBLICATIONS

Griffith, et al., "Chemical Abstracts", vol. 101, 1984, Col. 101:55060d.
Böhme, et al., "Chem. Ber.", vol. 105, 1972, pp. 1578–1585.

Primary Examiner—Richard L. Raymond
Assistant Examiner—James H. Turnipseed
Attorney, Agent, or Firm—Jacobs & Jacobs

[57] ABSTRACT

A compound of formula 1, or a solvate or salt thereof:

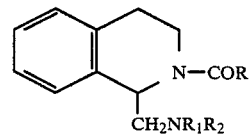

I in which: RCO is an acyl group in which the group R comprises a substituted or unsubstituted carbocyclic or heterocyclic aromatic ring and $R_1$ and $R_2$ are independently $C_{1-6}$ alkyl groups or together form a $C_{3-6}$ polymethylene or alkenylene group, is useful for treating pain.

9 Claims, No Drawings

ISOQUINOLINE DERIVATIVES, ANALGESIC COMPOUNDS THEREOF AND METHOD OF TREATING PAIN

This invention is concerned with novel isoquinoline derivatives, processes for their preparation, and their use in medicine, particularly as analgesics.

Compounds which are K-receptor agonists act as analgesics through interaction with Kappa opioid receptors. The advantage of K-receptor agonists over the classical μ-receptor agonists, such as morphine, lies in their ability of causing analgesia while being devoid of morphine-like behavioural effects and addiction liability.

We have now discovered a novel class of compounds which exhibit K-receptor agonism without some of the behavioural effects of morphine and morphine analogues, and which are thus of potential therapeutic utility as analgesics.

According to the present invention there is provided a compound, or a solvate or salt thereof, of formula I:

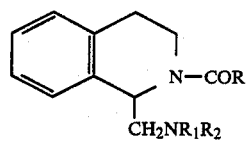

I in which: RCO is an acyl group in which the group R comprises a substituted or unsubstituted carbocyclic or heterocyclic aromatic ring and $R_1$ and $R_2$ are independently $C_1$-$C_6$ alkyl groups or together form a $C_{3-6}$ polymethylene or alkenylene group. As an alkyl group, each of $R_1$ and $R_2$ may be methyl, ethyl, propyl, butyl, pentyl or hexyl, preferably methyl.

As a polymethylene group, each of $R_1$ and $R_2$ may be propylene, butylene, pentylene or hexylene, and is preferably butylene. As an alkenylene group, $R_1$-$R_2$ may be typically —$CH_2$—CH=CH—$CH_2$—.

The group R preferably has the formula II

   II in which n is 0, 1 or 2, m is 0, 1 or 2,

X is a direct bond, or O, S or $NR_4$ in which $R_4$ is hydrogen or $C_{1-6}$ alkyl, Ar is a substituted or unsubstituted carbocyclic or heterocyclic ring, $R_3$ is an electron withdrawing substituent, or an alkyl, aryl, aralkyl, hydroxy or alkoxy group, or together with another $R_3$ group forms a carbocyclic ring.

Examples of electron withdrawing substituents include halogen, preferably chloro or bromo, —$CF_3$, —$NO_2$, —CN, —$SO_3H$, —$SO_2NR_5R_6$, —$CO_2R_7$, —$COR_8$ or —$CONR_9R_{10}$ wherein each of $R_5$ to $R_{10}$ independently represents hydrogen, alkyl or aryl.

Typically Ar is phenyl or 2- or 3-thienyl and is preferably substituted by one or more halogens, typically chlorine or bromiine or one or more —$NO_2$, —CN or —$CF_3$ groups. Preferably the substituents are in the meta and/or para positions on the phenyl ring.

X is typically oxygen or a direct bond, and n is typically 0 or 1.

Suitable examples of R are:

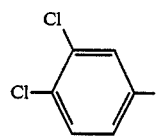

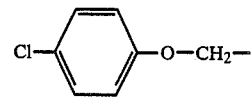

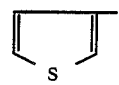

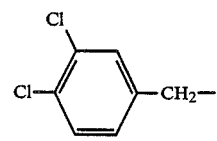

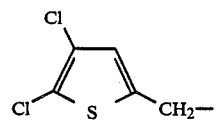

The compounds of formula I or their salts or solvates are preferably in pharmaceutically acceptable or substantially pure form. By pharmaceutically acceptable form is meant, inter alia, of a pharameutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicyclic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates.

The present invention also provide a process for the preparation of a compound of formula I which comprises reacting a compound of formula III

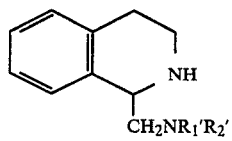   III in which $R_1'$ and $R_2'$ are $R_1$ and $R_2$ as defined for formula I or a group or atom convertible to $R_1$ and $R_2$, with a compound of formula R'CO.OH or an active derivative thereof, in which R' is R as defined for formula I or a group convertible to R, to form a compound of formula Ia

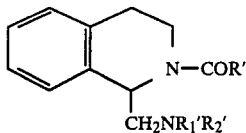
Ia and then performing one or more of the following steps:

(a) where R', $R_1'$ or $R_2'$ are other than R, $R_1$ and $R_2$, converting R', $R_1'$ or $R_2'$ to R, $R_1$ or $R_2$ to obtain a compound of formula I, (b) where R', $R_1'$ and $R_2'$ are R, $R_1$ and $R_2$, converting one R, $R_1$ or $R_2$ to another R, $R_1$ or $R_2$ to obtain a compound of formula I, (c) forming a salt and/or solvate of the obtained compound of formula I.

Suitable active derivatives of R'CO.OH are acid chlorides or acid anhydrides. Another suitable derivative is a mixed anhydride formed between the acid and an alkyl chloroformate.

For example, in standard methods well known to those skilled in the art, the compound of formula III may be coupled:

(a) with an acid chloride in the presence of an inorganic or organic base, (b) with the acid in the presence of dicyclohexyl carbodiimide, N-dimethylaminopropyl-N'-ethyl carbodiimide or carbonyl diimidazole, (c) with a mixed anhydride generated in situ from the acid and an alkyl (for example ethyl) chloroformate.

It will be appreciated that a compound of formula Ia may be converted to a compound of formula I, or one compound of formula I may be converted to another compound of formula I, by interconversion of suitable substituents. Thus certain compounds of formula I and Ia are useful intermediates in forming other compounds of the present invention.

$R_1'$ and $R_2'$ may be alkyl groups and converted to $R_1'/R_2'$ hydrogen atoms by conventional amine dealkylation. When $R_1'$ or $R_2'$ is benzyl or substituted benzyl it may be converted to an $R_1'$ or $R_2'$ hydrogen atom by catalytic hydrogenation or other method of reduction. $R_1'$ and $R_2'$ as hydrogen atoms may be converted to $R_1$ and $R_2$ alkyl groups by conventional amine alkylation. $R_1'$ and $R_2'$ are preferably $R_1$ and $R_2$ respectively.

The compound R'CO.OH is typically of the formula IIa

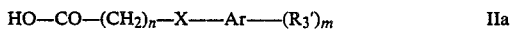
IIa in which $R_3'$ is $R_3$ as defined for formula II or a group or atom convertible to $R_3$, the other variables being as defined for formula II. A preferred reagent is the equivalent acid halide of formula IIb

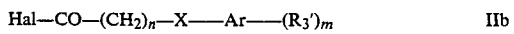
IIb in which Hal is a halogen, typically chlorine or bromine.

Conversions of substituents $R_3'$ on the aromatic group Ar to obtain $R_3$ are generally known in the art of aromatic chemistry. $R_3'$ is preferably $R_3$.

The compounds of formula I may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

The compounds of formula I exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

The compound of formula III may be obtained by catalytic hydrogenation of a compound of formula IV, for example by hydrogenation in ethanol in the presence of a palladium catalyst supported on carbon.

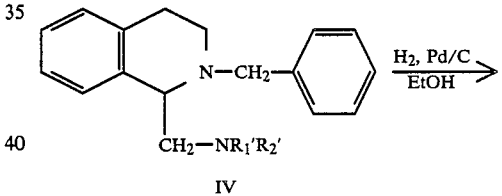
IV

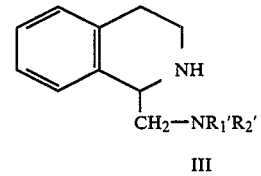
III

Alternatively, a compound of formula (III) may be obtained from the known compound 1-chloromethyl-3,4-dihydroisoquinoline by treatment with an amine of formula NHR$_1'$R$_2'$, where $R_1'$ and $R_2'$ are as defined above, followed by reaction of the formed compound of formula (V) with NaBH$_4$ or with hydrogen in the presence of a 5% palladium on charcoal catalyst, in accordance with the following reaction scheme:

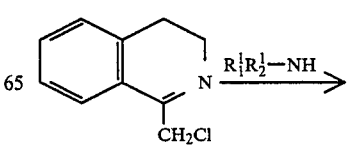

-continued

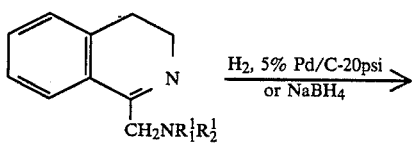
(V)

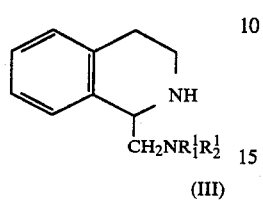
(III)

-continued

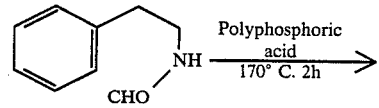

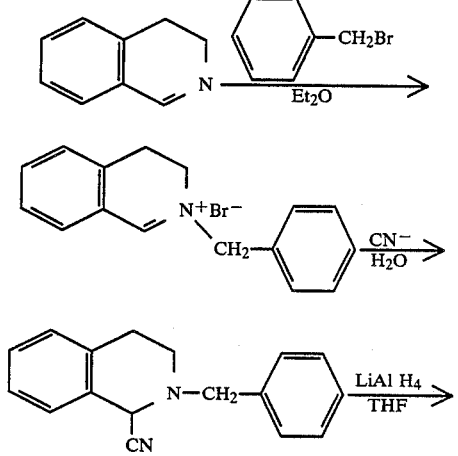

Compounds of formula IV in which $R_1'$ and $R_2'$ are not hydrogen may be derived from the compound of formula IV in which $R_1'$ and $R_2'$ are both hydrogen. For example compounds in which $R_1'$ and $R_2'$ are methyl or together form a pyrrolidine ring may be obtained as follows:

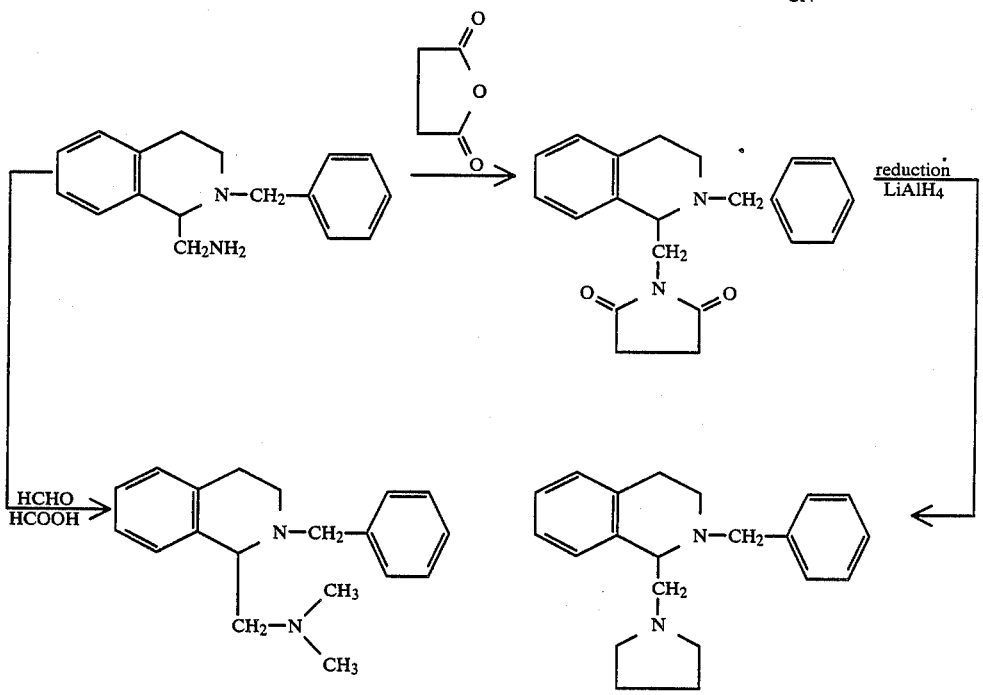

Other compounds of formula IV may be obtained by analogous procedures.

The compound of formula IV in which $R_1'$ and $R_2'$ are hydrogen may be prepared from phenylethylamine by the following illustrative reaction scheme, which uses conventional procedures:

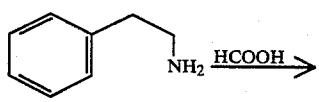

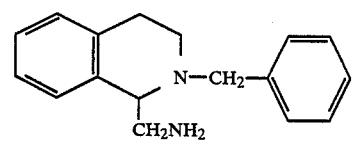

Certain intermediates described above are novel compounds and, together with the described processes for their preparation, they form a further aspect of this invention.

The activity of the compounds of formula I in standard analgesic tests indicates that they are of therapeutic utility in the treatment of pain.

Accordingly the present invention also provides a compound of formula I, or a pharmaceutically acceptable salt or solvate thereof, for use as an active therapeutic substance.

The present invention further provides a pharmaceutical composition comprising a compound of formula I, or a pharmaceutically acceptable salt or solvate thereof, and a pharmaceutically acceptable carrier.

The present invention also provides the use of a compound of formula I, or a pharmaceutically acceptable salt or solvate thereof, in the manufacture of a medicament of the treatment of pain.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents.

Preferably, a pharmaceutical composition of the invention is in unit dosage form and in a form adapted for use in the medical or verterinary fields. For example, such preparations may be in a pack form accompanied by written or printed instructions for use as an agent in the treatment of pain.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminum stearate gel, hydrogenated edible fats; emulsifying agents, for example lecithin, sorbitan monooleate, or acacia, aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. This may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method of treating pain in mammals, particularly in humans, which comprises administering an effective amount of a compound of formula (I) or a pharmaceutically acceptable salt or solvate thereof, to a sufferer.

Compounds of this invention and their preparation are illustrated in the following Examples.

EXAMPLE 1

(a)
2-benzyl-1-dimethylaminomethyl-1,2,3,4-tetrahydroiso-quinoline 11 g of 1-aminomethyl-2-benzyl-1,2,3,4-tetrahydroiso-quinoline (known compound, for instance J. Med. Chem. 26, 507/1983) were dissolved in 70 ml of 70% formic acid, and 30 ml of 40% formaldehyde and 2.5 g sodium formate were added to the solution. After refluxing for 8 hours, 2.5 g of sodium formate, 20 ml of 85% formic acid and 10 ml of 10% formaldehyde were added, and reflux was continued for 8 more hours. After evaporation i.v., the residue was distilled collecting the fraction boiling at 134°–45° C. at 0.4 mmHg.

10.8 g were obtained, sufficiently pure for the subsequent step.

(b)
1-dimethylaminomethyl-1,2,3,4-tetrahydroiso-quinoline 10.5 g of 2-benzyl-1-dimethylaminomethyl-1,2,3,4-tetrahydroisoquinoline were dissolved in 250 ml of 95% ethanol, 1.8 g of 5% Pd on charcoal were added, and the mixture was hydrogenated at room pressure and temperature for 4 hours. After filtration, and evaporation i.v., 7 g of product were obtained, sufficiently pure for the subsequent step.

(c)
1-dimethylaminomethyl-2-(3,4-dichlorophenyl)-acetyl-1,2,3,4-tetrahydroisoquinoline hydrochloride 2.3 g (12.1 mmoles) of 1-dimethylaminomethyl-1,2,3,4-tetrahydroisoquinoline and 2.8 g (13.31 mmoles) of 3,4-dichlorophenylacetic acid were dissolved in 45 ml of dry chloroform and cooled to −100° C. 4 g of dicyclohexylcarbodiimide dissolved in 15 ml of dry chloroform were added dropwise to the stirred solution, and the mixture brought to room temperature and stirred for 5 hours. After completion of the reaction (as confirmed by TLC), the precipitated dicyclohexylurea was removed by suction filtration, and the solution evaporated to dryness in vacuo. The residue was suspended in water and brought to acidic pH with 37% hydrochloric acid. The white solid formed was filtered and washed many times with ethanol. The combined mother liquor and washings were evaporated to dryness in vacuo and the solid residue was crystallized from absolute ethanol/methanol (1/1).

| Yield | 3.75 g |
|---|---|
| M.P. | 280° C. |
| M.W. | 413.774 |
| Molecular Formula | $C_{20}H_{22}N_2OCl_2 \cdot HCl$ |

A sample of the salt was dissolved in water, the solution made alkaline by adding aqueous $Na_2CO_3$, the precipitate extracted in ether. The base obtained by evaporation of ether gave an NMR spectrum identical with that of Example 3 (levo rotatory enantiomer). The melting point of the base was 107°–8° C. (crystallized from ethyl acetate).

EXAMPLE 2

(+)-1-dimethylaminomethyl-2-(3,4-dichlorophenyla-cetyl -1,2,3,4-tetrahydroisoquinoline-(+)-tartrate ethanolate hemihydrate 5.5 g (0.0145 moles) of 1-dimethylaminomethyl-2-(3,4-dichlorophenylacetyl)-1,2,3,4-tetrahydroisoquinoline base were dissolved in 60 ml of hot absolute ethanol, and 2.4 g (0.0160 moles) of L(+) tartaric acid were added. On slow cooling 2.84 g of tartrate precipitated, which were collected and crystallized from 60 ml of ethanol.

Yield 2.5 g
$C_{20}H_{22}Cl_2N_2O \cdot C_4H_5O_5 \cdot C_2H_5OH \cdot 0.5H_2O$
MW 582.47
M.P. 157°–9° C.
$[\alpha]^{20}D = +50.13$ (C=1. MeOH)

A sample of base was prepared from the tartrate by dissolving in water, alkalizing and extracting in ether. It had an $[\alpha]^{20}D = +60.13$ (C=1, CHCl$_3$) The NMR spectrum of the base was identical to that of the levo-rotatory enantiomer (Example 3).

EXAMPLE 3

(−)-1-dimethylaminomethyl-2-(3,4-dichlorophenyl)-1,2,3,4-tetrahydroisoquinoline-(−)-tartrate ethanolate hemihydrate 6.1 g (0.016 moles) of 1-dimethylaminomethyl-2-(3,4-dichlorophenylacetyl)-1,2,3,4-tetrahydroisoquinoline base and 2.7 g (0.018 moles) of D-(−)-tartaric acid were dissolved in 180 ml of hot absolute ethanol. The tartrate, which precipitated on slow cooling, was collected and crystallized from 110 ml of ethanol.

Yield 3.6 g
$C_{20}H_{22}Cl_2N_2O \cdot C_4H_6O_6 \cdot C_2H_5OH \cdot 0.5H_2O$
MW 582.47
M.P. 157°–9° C.
$[\alpha]^{20}D = -49.75$ (C=1, MeOH)

A sample of base was prepared from the salt by dissolving in water, alkalizing and extracting in ether.
It had an $[\alpha]^{20}D = -59.86$. NMR of the base (CDCl$_3$-90 MHz).

| NMR δ = | 2.37 | s | 3H |
|---|---|---|---|
| | 2.40 | s | 3H |
| | 2.45–3.10 | m | 4H |
| | 3.35–4.15 | m | 3H |
| | 4.65–5.10 | m | 1H |
| | 5.80 | dd | 1H |
| | 7.00–7.50 | m | 7H |

EXAMPLE 4

2-(4-bromophenylacetyl)-1-dimethylaminomethyl-1,2,3,4-tetrahydroisoquinoline hydrochloride Prepared as Ex. No. 1 by coupling 800 mg of 1-dimethylaminomethyl-1,2,3,4-tetrahydroisoquinoline and 1.05 g of (4-bromophenylaceticacid, dissolved in 35 ml of CH$_2$Cl$_2$, in the presence of 1.3 g of dicyclohexylcarbodiimide.

Yield 1.1 g
$C_{20}H_{24}BrClN_2O$
MW 423.781
M.P. 283°–6° C. (from 95% Ethanol)

EXAMPLE 5

1-dimethylaminomethyl-2-(nitrophenylacetyl)-1,2,3,4-tetrahydroisoquinoline hydrochloride hemihydrate Prepared as Ex. No. 1 from 800 mg of 1-dimethylaminomethyl-1,2,3,4-tetrahydroisoquinoline, 900 mg of 4-nitrophenylacetic acid and 1.4 g of dicyclohexylcarbodiimide in 35 ml of $CH_2Cl_2$.

Yield 1.2 g
$C_{20}H_{25}ClN_3O_{3.5}$
MW 398.881
M.P. 236°–8° C. (from abs. ethanol/ether)

EXAMPLE 6

1-dimethylaminomethyl-2-(2-nitrophenylacetyl)-1,2,3,4-tetrahydroisoquinoline hydrochloride hemihydrate Prepared as Ex. No. 1 from 900 mg of 1-dimethylaminoethyl-1,2,3,4-tetrahydroisoquinoline, 900 mg of 4-nitrophenylacetic acid and 1.4 g of dicyclohexylcarbodiimide in 40 ml of $CH_2Cl_2$.

Yield 1.4 g
$C_{20}H_{25}ClN_3O_{3.5}$
MW 398.881
M.P. 263°–5° C. (from abs. ethanol)

EXAMPLE 7

(a)

2-benzyl-1-[1(2,5-dioxopyrrolidinylmethyl)]-1,2,3,4-tetrahydroisoquinoline 5 g of 1-aminomethyl-2-benzyl-1,2,3,4-tetrahydroisoquinoline (J. Med. Chem. 26, 507/1983) and 2 g of succinic anhydride were suspended in 20 ml of tetraline, and the mixture kept 1 hr. at 140° C. The reaction mixture was cooled, the liquid phase was decanted from a glassy precipitate and distilled at 45° C./0.5 mmHg. in order to eliminate tetraline. The residue was triturated in hexane/ethyl acetate and filtered. Yield 4 g (b)

2-benzyl-1-[1-pyrrolidinylmethyl)-1,2,3,4-tetrahydroisoquinoline

The product of the foregoing step (3.5 g) was dissolved in 60 ml of dry toluene, and 15 ml of a 70% toluene solution of sodium bis(2-methoxyethoxy)aluminium hydride (Vitride) were dropped into the solution at room temperature under stirring. The solution was kept 0.5 hr at room temperature and 3 hr at 80° C. After cooling, it was cautiously quenched with 15 ml of ION NaOH, the organic layer was separated, washed with water, dryed on $Na_2SO_4$, evaporated i.v. 3.4 g of sufficiently pure oil were obtained. A sample was dissolved in ethyl acetate, and the dihydrochloride was precipitated by addition of HCl/ether. M.P. 200° C.

(c)

1-[1-pyrrolidinylmethyl)-1,2,3,4-tetrahydroisoquinoline 8 g of 2-benzyl-1-(1-pyrrolidinylmethyl)-1,2,3,4-tetrahydroisoquinoline were dissolved in 200 ml of 95% ethanol and hydrogenated on 1.5 g of 5% Pd on charcoal at 40° C. and room temperature. After 7 hr the catalyst was filtered off, and the solvent evaporated i.v. 5.5 g of crude product were obtained, sufficiently pure for the subsequent step.

(d)

1-[1-pyrrolidinylmethyl)-2-(3,4-dichlorophenylacetyl)-1,2,3,4-tetrahydroisoquinoline hydrochloride Prepared as Ex. No. 1 from 1.9 g of 1-(1-pyrrolidinylmethyl)-1,2,3,4-tetrahydroiso-quinoline, 2.g of 2,2-dichlorophenylacetic acid and 3 g of dicyclohexylcarbodiimide in 55 ml of $CH_2Cl_2$.

Yield 1.7 g
$C_{22}H_{25}Cl_3N_2O$
MW 439.807
MP 253°–7° C.

A sample of free base gave an NMR spectrum identical to that of the two levo rotatory enantiomer (Example 9)

EXAMPLE 8

(+)-1-[1-pyrrolidinylmethyl)-2-(3,4-dichlorophenylacetyl)-1,2,3,4-tetrahydroisoquinoline (+)-tartrate 6 g of the compound of Ex. No. 7(d) were transformed into the free base by dissolution in water, treatment with $Na_2CO_3$, extraction in either, and evaporation of the ether. 5.4 g of the obtained free base were dissolved in absolute ethanol together with 2.28 g of L(+)-tartaric acid. The solution was evaporated to dryness, and the residue taken up in 160 ml of hot acetone. After filtering off a little insoluble matter, and 3 days standing, 2.9 g of precipitate were obtained. They were crystallized from 650 ml of acetone.

Yield 1.5 g
$C_{22}H_{24}Cl_2N_2O \cdot C_4H_6O_6$
MW 553.43
MP 185°–7° C.
$[\alpha]^{20}D = +55.01$ (C=1. MeOH)

A sample of tartrate salt was transformed into the free base by dissolving in water, treatment with $Na_2CO_3$, extraction in ether, and evaporation of ether. The base gave an $[\alpha]^{20}D = +58.01$ (C=1 $CHCl_3$). The base gave an NMR spectrum identical to that of the laevorotatory enantiomer.

EXAMPLE 9

(−)-1-[1-pyrrolidinylmethyl)-2-(3,4-dichlorophenylacetyl)-1,2,4-tetrahydroisoquinoline (−)-tartrate The compound of the foregoing example in other liquors (acetone) were evaporated to dryness. The solid residue was dissolved in water, alkalized with NaOH; the precipitate was extracted in ether, and the ether evaporated to dryness, leaving 4.1 g of free base, enriched in the laevo-rotatory enantiomer. The base was dissolved in 100 ml of absolute ethanol, and 1.68 g of D(−) tartaric acid, dissolved in the minimum amount of ethanol were added. The precipitate was crystallized twice from 300 ml and 750 of acetone, respectively.

Yield 1.4 g
$C_{22}H_{24}Cl_2N_2O \cdot C_4H_4O_6$
MW 553.43
MP 185°–7° C.
$[\alpha]^{20}D = -54.25$ (C=1, MeOH)

A sample of tartrate salt was transformed into the base in the usual way. The free base had an $[\alpha]^{20}D = -60.25$ (C)=1, $CHCl_3$).

NMR of the base ($CDCl_3$—90 MHZ)

| | | |
|---|---|---|
| δ = 1.65–1.85 | m | 4H |

| | | |
|---|---|---|
| 2.30–3.10 | m | 8H |
| 3.40–4.10 | m | 3H |
| 4.60–5.15 | m | 1H |
| 5.90 | dd | 1H |
| 7.00–7.50 | m | 7H |

The compounds of the following examples were prepared by the same procedure as Ex. No. 1, by coupling 800 mg (0.0037 moles) of 1-(1-pyrrolidinylmethyl)-1,2,3,4-tetrahydroisoquinoline and 0.004 moles of the appropriate substituted phenylacetic acid in 50 ml of $CH_2Cl_2$, in the presence of 0.93 g (0.0045 moles) of dicyclohexylcarbodiimide.

EXAMPLE 10

1-(1-pyrrolidinylmethyl)-2-(4-bromophenylacetyl)-1,2,3,4-tetrahydroisoquinoline hydrochloride From 4-bromophenylacetic acid.

EXAMPLE 11

1-(1-pyrrolidinylmethyl)-2-(4-nitrophenylacetyl)-1,2,3,4-tetrahydroisoquinoline hydrochloride hemihydrate From 4-nitrophenylacetic acid.

EXAMPLE 12

1-(1-pyrrolidinylmethyl)-2-(3-nitrophenylacetyl)-1,2,3,4-tetrahydroisoquinoline hydrochloride hydrate From 3-nitrophenylacetic acid.

EXAMPLE 13

1-(1-pyrrolidinylmethyl)-2-(2-nitrophenylacetyl)-1,2,3,4-tetrahydroisoquinoline hydrochloride hemihydrate From 2-nitrophenylacetic acid.

EXAMPLE 14

1-(1-pyrrolidinylmethyl)-2-(4-trifluoromethylacetyl)-1,2,3,4-tetrahydroisoquinoline hydrochloride From 4-trifluoroethylphenylacetic acid.

| NMR ($CDCl_3$ - 80 MHZ) | | | |
|---|---|---|---|
| $\delta =$ 1.65–2.30 | m | | 4H |
| 2.30–3.30 | m | | 5H |
| 3.30—3.30 | m | | 5H |
| 4.10 | AB system, | J = 15 | 2H |
| 6.10 | dd | J = 12 and 5 | 1H |
| 6.75–7.70 | m | | 8H |
| 11.7 | broad s | | 1H |

EXAMPLE 15

1-(1-pyrrolidinylmethyl)-2-(4-cyanophenylacetyl)-1,2,3,4-tetrahydroisoquinoline hydrochloride sesquihydrate From 4-cyanophenylacetic acid

| NMR ($CDCl_3$ - 80 MHZ) | | | |
|---|---|---|---|
| $\delta =$ 1.80–2.40 | m | | 4H |
| 2.40–3.30 | m | | 5H |
| 3.40–4.45 | m | | 5H |
| 4.15 | AB system, | J = 15 | 2H |
| 6.10 | dd | J = 11.37 and 4.5 | 1H |
| 6.9–7.65 | m | | 8H |
| 11.7 | broad s | | 1H |

The structures and physical/chemical data for the compounds of the Examples are summarised in Table 1

TABLE I

General formula

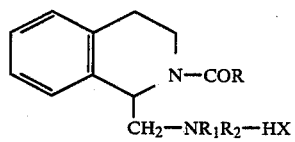

| Example Nos. | R | R1,R2 | SALT | MOL. FORMULA | MOL. WEIGHT | M.P.(°C.) | ISOMERISM |
|---|---|---|---|---|---|---|---|
| 1 | —CH₂—(2,4-diCl-phenyl) | R1=R2= CH₃ | HCl | $C_{20}H_{23}Cl_3N_2O$ | 413.77 | 280 | Racemate |
| 2 | —CH₂—(2,4-diCl-phenyl) | R1=R2= CH₃ | (+)Tartrate EtOH.0.5 H2O | $C_{26}H_{35}Cl_2N_2O_{8.5}$ | 582.47 | 157–9 | (+)enantiomer of Ex.1 $[\alpha]_D^{20} = +50.13$ (MeOH C=1) |
| 3 | —CH₂—(2,4-diCl-phenyl) | R1=R2= CH₃ | (−)Tartrate EtOH.0.5 H2O | $C_{26}H_{35}Cl_2N_2O_{8.5}$ | 582.47 | 157–9 | (−)enantiomer of Ex.1 $[\alpha]_D^{20} = -49.75$ (MeOH C=1) |
| 4 | —CH₂—(4-Br-phenyl) | R1=R2= CH₃ | HCl | $C_{20}H_{24}BrClN_2O$ | 423.781 | 283–6 | Racemate |
| 5 | —CH₂—(4-NO₂-phenyl) | R1=R2= CH₃ | HCl.0.5 H2O | $C_{20}H_{25}ClN_3O_{3.5}$ | 398.881 | 236–8 | Racemate |

TABLE I-continued

General formula

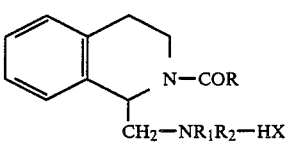

| Example Nos. | R | R1,R2 | SALT | MOL. FORMULA | MOL. WEIGHT | M.P(°C.) | ISOMERISM |
|---|---|---|---|---|---|---|---|
| 6 | $-CH_2-\text{C}_6\text{H}_4-NO_2$ (o) | R1=R2=CH3 | HCl 0.5 H2O | $C_{20}H_{25}ClN_3O_{3.5}$ | 398.881 | 263–5 | Racemate |
| 7 | $-CH_2-\text{C}_6\text{H}_3-Cl_2$ (2,3) | R1R2= | HCl | $C_{22}H_{25}Cl_3N_2O$ | 439.807 | 253–7 | Racemate |
| 8 | $-CH_2-\text{C}_6\text{H}_3-Cl_2$ | R1R2= | (+)tartrate | $C_{26}H_{30}Cl_2N_2O_7$ | 553.43 | 185–7 | (+)enantiomer of Ex.2 $[\alpha]_D^{20}=+55.01$ (MeOH C=1) |
| 9 | $-CH_2-\text{C}_6\text{H}_3-Cl_2$ | R1R2= | (−)tartrate | $C_{26}H_{30}Cl_2N_2O_7$ | 553.43 | 185–7 | (+)enantoimer of Ex.2 $[\alpha]_D^{20}=-54.25$ (MeOH C=1) |
| 10 | $-CH_2-\text{C}_6\text{H}_4-Br$ | R1R2= | HCl | $C_{22}H_{26}BrClN_2O$ | 449.817 | 285–7 | Racemate |
| 11 | $-CH_2-\text{C}_6\text{H}_4-NO_2$ | R1R2= | HCl.0.5 H2O | $C_{22}H_{27}ClN_3O_{3.5}$ | 424.91 | 148–51 | Racemate |
| 12 | $-CH_2-\text{C}_6\text{H}_4-NO_2$ (m) | R1R2= | HCl.H2O | $C_{22}H_{28}ClN_3O_4$ | 433.925 | 118–21 | Racemate |
| 13 | $-CH_2-\text{C}_6\text{H}_4-NO_2$ | R1R2= | HCl.0.5 H2O | $C_{22}H_{27}ClN_3O_{3.5}$ | 424.91 | 276–9 | Racemate |
| 14 | $-CH_2-\text{C}_6\text{H}_4-CF_3$ | R1R2= | HCl | $C_{23}H_{26}ClF_3N_2O$ | 438.91 | 277–80 | Racemate |
| 15 | $-CH_2-\text{C}_6\text{H}_4-CN$ | R1R2= | HCl.1.5 H2O | $C_{23}H_{29}ClN_3O_{2.5}$ | 422.943 | 178 | Racemate |

The pharmacological activity of the compounds of this invention is illustrated by various in vitro and in vivo models, using the following test procedures, in which the mouse tail flick test demonstrates analgesic activity.

The results of the tests are given in Table 2

Mouse Tail-flick test (Modified from the procedure published by D'Amour et al., J. Pharm. Exptl. Ther.72, 74/1941).

Male Charles River mice, average weight 26 g, are used. Selection is carried out before beginning of experiments: only mice whose reaction time is less than 8 sec are used. They are randomly distributed into groups of 10 and dosed with compounds under test, with positive and negative controls being included.

Compounds under test are administered subcutaneously in isotonic saline in a volume of 20 ml. $Kg^{-1}$. 30 min later mice are placed again under heat source (Socrel apparatus) and reaction time is recorded.

The analgesic activity of the test compound is expressed as the percent number of mice doubling the initial time within a group.

$$\% \text{ analgesia} = \frac{\text{No. of mice doubling the reaction time}}{\text{Total no. of mice per group}} \times 100$$

RECEPTOR AFFINITY STUDY

Tissue preparation

Radio receptor binding to μ and K sites is performed on fresh guinea pig brain homogenate prepared according to Kosterlitz. (1981).

Whole brain without cerebellum is homogenized in 50 mM, Tris-buffer (pH 7.4 at 0° C.) and centrifuged at 49,000×g×10 min.

The pellet is then resuspended in the same buffer, incubated at 37° C. for 45 min. and centrifuged again.

1.9 ml of the final homogenate (1:100 in Tris-pH 7.4, 0° C.) is used for the binding assay.

Binding to μ sites (Magnan J., 1982)

$^3$H[D—Ala$^2$, MePhe$^4$, Gly—ol$^5$] Enkephalin ($^3$H-DAGO), an enkephalin analogue that binds selectively to μ receptor, is added to the biological substrate and incubated at 25° C. for 40 min., filtered through Whatman GF—C and washed with ice-cold Tris-buffer.

The filters are then dryed, solubilized in Filtercount and the radioactivity monitored. Non specific binding is determined in the presence of $10^{-6}$M Naloxone.

Binding to K sites (Magnan J., 1982)

The binding of tritiated Ethylketocyclazocine to brain homogenate is measured in the presence of 100 nanomolar D—Ala—D—LeuEnkephalin (DADLE) and 100 nanomolar DAGO, added to saturate the δ and μ opioid receptors respectively.

Final homogenate with solutions of the cold ligand and of the labelled ligand is incubated for 40 min. at 25° C., filtered through Whatman GF/C glass filter discs and washed.

The radioactivity bound to the filters is counted by liquid scintillation spectrophotometry.

MR 2266.500 nM is utilized to determine the saturable binding.

For the calculation of the kinetic parameters of the binding of labelled and unlabelled ligands, the equilibrium dissociation constant ($K_D$), the inhibition constant (Ki) and the maximum number of binding sites (B max) are determined from saturation curves and competition experiments (Hill 1910; Scatchard 1949; Cheng and Prusoff 1973); Gillan et al. 1980).

A concentration of radioligand near $K_D$ is used in the binding assays evaluating our compounds.

Hill, A. V. (1910): J. Physiol. 40, IV-VIII (1910)

Scatchard G. (1949): Ann. N.Y. Acad. Sci., 51, 660-674

Cheng and Prusoff W. H. (1973): Biochem. Pharmac. 22, 3099-3102

Gillan M. G. C., Kosterlitz H. W.: Br.J. Pharmac, 70, and Paterson S. Y. (1980) 481-490

Kotsterliz H. W., Paterson S. Y.: Br.J. Pharmac. 73, and Robson L. E. (1981) 934-949

Magnan J., Paterson S. Y.,: Arch. Pharmacol. 319, Tavani A., and Kosterlits 197-205 H. W. (1982)

TABLE 2
PHARMACOLOGICAL DATA

| Example Nos. | IN VIVO TESTS -ED$_{50}$ mg Kg$^{-1}$ s.c MOUSE TAIL FLICK | RECEPTOR BINDING -K$_i$ (nM) | |
|---|---|---|---|
| | | μ | K |
| 1 | 0.041 | 415 | 1.59 |
| 3 | 0.032 | 286 | 2.37 |
| 4 | 0.25 | 597 | 3.19 |
| 5 | 0.23 | 655 | 5.72 |
| 6 | — | >10000 | 30.6 |
| 7 | 0.016 | 40.2 | 0.84 |
| 8 | — | 5000 | 500 |
| 9 | 0.009 | 30.2 | 0.43 |
| 10 | 0.031 | 50 | 0.57 |
| 11 | 0.016 | 62 | 0.64 |
| 12 | 0.23 | — | — |
| 13 | — | 1852 | 7.94 |
| 14 | 0.33 | — | — |
| 15 | 70% protection at 1 mg/kg | | |

We claim:

1. A compound of formula 1, or a solvate or salt thereof:

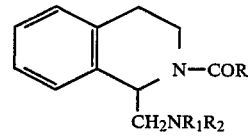

I in which:

R is a group of formula—(CH$_2$)n—X——Ar——(R$_3$)m in which n is 0, 1 or 2, m is 0, 1 or 2, X is a direct bond, or O, S or NR$_4$ in which R$_4$ is hydrogen or C$_{1-6}$ alkyl, Ar is phenyl or thienyl, R$_3$ is an electron withdrawing substituent selected from the group consisting of halogen, —CF$_3$, —NO$_2$, —CN, —SO$_3$H, —SO$_2$NR$_5$R$_6$, —CO$_2$R$_7$, —COR$_8$ and —CONR$_9$R$_{10}$ wherein R$_5$ to R$_{10}$ represent hydrogen or C$_{1-6}$ alkyl, or R$_3$ is an alkyl, aryl, aralkyl, hydroxy or alkoxy group, or together with another R$_3$ group forms a carbocyclic ring; and R$_1$ and R$_2$ are independently C$_{1-6}$ alkyl groups or together form a C$_{3-6}$ polymethylene or alkenylene group.

2. A compound according to claim 1, in which each of R$_1$ and R$_2$ is methyl, ethyl, propyl, butyl, pentyl or hexyl.

3. A compound according to claim 1, in which R$_1$ and R$_2$ together form a propylene, pentylene or hexylene group, or a —CH$_2$—CH═CH—CH$_2$—group.

4. A compound according to claim 1, in which R$_3$ is halogen, —CF$_3$, —NO$_2$, —CN, —OS$_3$H, —SO$_2$NR$_5$R$_6$, —CO$_2$R$_7$, —COR$_8$ or —CONR$_9$R$_{10}$ wherein each of R$_5$ to R$_{10}$ independently represents hydrogen, alkyl or aryl.

5. A compound according to claim 1, in which Ar is phenyl,

6. A compound selected from the group consisting of; 1-dimethylaminomethyl-2-(3,4-dichlorophenyl)-acetyl-1,2,3,4-tetrahydroisoquinoline hydrochloride, (+)-1-dimethylaminomethyl-2-(3,4-dichlorophenylacetyl)-1,2,3,4-tetrahydroisoquinoline-+-tartrate ethanolate hemihydrate, (−)-1-dimethylaminomethyl-2-(3,4-dichlorophenyl)-1,2,3,4-tetrahydroisoquinoline-(−)-tartrate ethanolate hemihydrate, 2-(4-bromophenylacetyl)-1-dimethylaminomethyl-1,2,3,4-tetrahydroisoquinoline hydrochloride, 1-dimethylaminomethyl-2-(nitrophenylacetyl)-1,2,3,4-tetrahydroisoquinoline hydrochloride hemihydrate, 1-dimethylaminomethyl-2-(2-nitrophenylacetyl)-1,2,3,4-tetrahydroisoquinoline hydrochloride hemihydrate, 1-(1-pyrrolidinylmethyl)-2-(3,4-dichlorophenylacetyl)]-1,2,3,4-tetrahydroisoquinoline hydrochloride, (+)-1-(1-pyrrolidinylmethyl)-2-(3,4-dichlorophenylacetyl)-1,2,3,4-tetrahydroisoquinoline (+)-tartrate, (−)-1-[1-pyrrolidinylmethyl)-2-(3,4-dichlorophenylacetyl)-1,2,3,4-tetrahydroisoquinoline (−)-tartrate, 1-(1-pyrrolidinylmethyl)-2-(4-bromophenylacetyl)-1,2,3,4-tetrahydroisoquinoline hydrochloride, 1-(1-pyrrolidinylmethyl)-2-(4-nitrophenylacetyl)-1,2,3,4-tetrahydroisoquinoline hydrochloride hemihydrate, 1-(1-pyrrolidinylmethyl)-2-(3-nitrophenylacetyl)-1,2,3,4-tetrahydroisoquinoline hydrochloride hydrate, 1-(1-pyrrolidinylmethyl)-2-(2-nitrophenylacetyl)-1,2,3,4-tetrahydroisoquinoline hydrochloride hemihydrate, 1-(1-pyrrolidinylmethyl)-2-(4-trifluoromethylacetyl)-1,2,3,4-tetrahydroisoquinoline hydrochloride, and 1-(1-prrolidinylmethyl)-2-(4-cyanophenylacetyl)-1,2,3,4-tetrahydroisoquinoline hydrochloride sesquihydrate.

7. A pharmaceutical composition comprising an analgesically effective amount of a compound according to claim 1, and a pharmaceutically acceptable carrier.

8. A composition according to claim 7 in unit dosage form.

9. A method of treating pain in mammals which comprises administering an effective, non-toxic amount of a compound according to claim 1 to a mammalian sufferer.

* * * * *